(12) United States Patent
Kemp et al.

(10) Patent No.: US 10,946,147 B2
(45) Date of Patent: Mar. 16, 2021

(54) CAP ASSEMBLY FOR COVERING A NEEDLE SHIELD AND METHOD FOR ASSEMBLING THE CAP ASSEMBLY

(71) Applicant: SANOFI-AVENTIS DEUTSCHLAND GMBH, Frankfurt am Main (DE)

(72) Inventors: Thomas Mark Kemp, Ashwell (GB); Louise Hodgson, Herts (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 110 days.

(21) Appl. No.: 15/736,645

(22) PCT Filed: Jun. 16, 2016

(86) PCT No.: PCT/EP2016/063866
§ 371 (c)(1),
(2) Date: Dec. 14, 2017

(87) PCT Pub. No.: WO2016/202916
PCT Pub. Date: Dec. 22, 2016

(65) Prior Publication Data
US 2018/0185589 A1    Jul. 5, 2018

(30) Foreign Application Priority Data
Jun. 18, 2015   (EP) .................................... 15172770

(51) Int. Cl.
*A61M 5/32*   (2006.01)
(52) U.S. Cl.
CPC ........ *A61M 5/3213* (2013.01); *A61M 5/3204* (2013.01); *A61M 5/3202* (2013.01); *A61M 2207/00* (2013.01); *A61M 2207/10* (2013.01)

(58) Field of Classification Search
CPC .............. A61M 5/3213; A61M 5/3204; A61M 2207/00; A61M 5/3202; A61M 2207/10
See application file for complete search history.

(56) References Cited

U.S. PATENT DOCUMENTS

| 5,098,400 A * | 3/1992 | Crouse ................ A61M 5/3204 604/192 |
| 8,834,415 B2 | 9/2014 | Schraga |

(Continued)

FOREIGN PATENT DOCUMENTS

| CN | 101489610 | 7/2009 |
| CN | 101939036 | 1/2011 |

(Continued)

OTHER PUBLICATIONS

International Search Report and Written Opinion in International Application No. PCT/EP2016/063866, dated Aug. 25, 2016, 12 pages.

(Continued)

*Primary Examiner* — Bradley J Osinski
(74) *Attorney, Agent, or Firm* — Fish & Richardson P.C.

(57) ABSTRACT

The disclosure refers to a cap assembly for covering a needle shield of an injection device, the cap assembly comprising: a collar, and a cap with a sheath and a bottom, wherein the collar is movable along a longitudinal direction relative to the sheath from an unlocked position not engaging the sheath towards a locked position, force-lockingly engaging the sheath, thereby locking the sheath to the needle shield.

12 Claims, 3 Drawing Sheets

(56) References Cited

U.S. PATENT DOCUMENTS

| | | | |
|---|---|---|---|
| 2011/0275992 A1 | 11/2011 | Abry et al. | |
| 2012/0232491 A1* | 9/2012 | Jennings | A61M 5/3202 604/192 |
| 2016/0175539 A1* | 6/2016 | Riedel | A61M 5/3204 604/192 |

FOREIGN PATENT DOCUMENTS

| | | |
|---|---|---|
| CN | 103608055 | 2/2014 |
| CN | 103764207 | 4/2014 |
| CN | 103974734 | 8/2014 |
| CN | 105530980 | 4/2016 |
| EP | 2489388 | 8/2012 |
| EP | 2878319 | 6/2015 |
| GB | 2438593 | 12/2007 |
| GB | 2465389 | 5/2010 |
| JP | 2009-538661 | 11/2009 |
| WO | WO 2007/138296 | 12/2007 |
| WO | WO 2009/087355 | 7/2009 |
| WO | WO 2012/103140 | 8/2012 |
| WO | WO 2013/006119 | 1/2013 |
| WO | WO 2013/058697 | 4/2013 |
| WO | WO 2015/007857 | 1/2015 |
| WO | WO 2016/202916 | 12/2016 |

OTHER PUBLICATIONS

International Preliminary Report on Patentability in International Application No. PCT/EP2016/063866, dated Dec. 19, 2017, 7 pages.

* cited by examiner

CAP ASSEMBLY FOR COVERING A NEEDLE SHIELD AND METHOD FOR ASSEMBLING THE CAP ASSEMBLY

CROSS REFERENCE TO RELATED APPLICATIONS

The present application is the U.S. national stage entry under 35 USC § 371 of International Patent Application No. PCT/EP2016/063866, filed on Jun. 16, 2016, which claims priority to European Patent Application No. 15172770.8, filed on Jun. 18, 2015, the entire contents of which are incorporated herein by reference.

TECHNICAL FIELD

The disclosure generally relates to a cap assembly for covering a needle shield that protects the needle of an injection device. The disclosure further relates to a method for assembling the cap assembly.

BACKGROUND

In order to protect the needle of an injection device such as an autoinjector, needle shields are known from the state of the art. It is also known to cover such needle shields with caps that mechanically protect the needle shield and the needle and that ease the removal of the needle shield from the needle in preparation of an injection.

SUMMARY

An improved assembly of a cap on a needle shield and an improved method of mounting a cap on a needle shield is described herein, in particularity as to reduce the amount of force required to exert on a needle shield when mounting the cap.

A cap assembly and a method for assembling a cap assembly are disclosed herein. Implementations can include one or more of the following features.

In the context of this specification, the terms distal and proximal are defined from the point of view of a person performing an injection. Consequently, a distal direction refers to a direction pointing towards the site of an injection and a distal end defines an end of an element that is directed towards the site of the injection. Respectively, the proximal end of an element or the proximal direction is directed away from the site of the injection and opposite to the distal end or distal direction.

According to the disclosure, a cap assembly for covering a needle shield of an injection device comprises at least a collar and a cap with a sheath and a bottom. The sheath substantially extends along a central longitudinal axis directed in a longitudinal direction from the proximal towards the distal end of the cap. On its proximal end, the cap has an opening aligned with the sheath. The distal end of the cap is at least partially closed by a bottom. The collar is movable relative to the sheath along the longitudinal direction. When moving the sheath relative to the collar, the collar is moved from an unlocked position into a locked position. In its unlocked position, the collar does not engage the needle shield or the sheath. In its locked position, the collar force-lockingly engages the sheath and thereby locks the sheath to the needle shield.

In some implementations, as an advantage, the needle shield is locked to the cap by moving the collar instead of moving the needle shield relative to the cap. In other words, the cap may be mounted onto the needle shield with substantially reduced or no force exerted on the needle shield while the needle shield is moved relative to the cap, thereby reducing the risk of damaging the needle or impacting sterility. Further, the needle shield is being removable upon removal of the cap.

In an embodiment of the cap assembly, the sheath is formed by radially deflectable arms proximally extending from the bottom. On the proximal ends of the radially deflectable arms, clips protrude radially inwardly towards the central longitudinal axis. The clips are adapted to be received by corresponding recesses in the outer surface of the needle shield. The collar circumferentially encloses the radially deflectable arms. In its unlocked position, the collar is sled towards the bottom of the cap. In its locked position, the collar is sled towards the proximal end of the cap such that the clips are form-fittingly held in the corresponding recesses. The collar may be held force-lockingly by friction, e.g. by an interference rib or a press fit, in its locked position.

By forcing apart the radially deflectable arms, the distal end of the needle shield can be introduced into the sheath formed by the radially deflectable arms without force. Once the clips face their corresponding recesses, the radially deflectable arms are released such that the clips form-fittingly engage the recesses. By sliding the collar proximally into its locked position, the collar engages the radially deflectable arms, thereby pressing the clips on the distal ends into the recesses. No force is exerted upon the needle shield along the longitudinal direction, thereby minimizing the risk of damaging the needle or loosening the needle shield or compromising sterility.

In an embodiment of the cap assembly, the clips are formed as catches pointing towards the proximal ends of the radially deflectable arms. In some embodiments, it is particularly easy to bring the clips into engagement with the recesses, as the catches snap into the recesses when the needle shield is introduced into the cap.

In an embodiment of the cap assembly, the sheath is formed as a rigid tube circumferentially enclosing the collar. The rigid tube is adapted to receive the needle shield with a tubular, proximally narrowing clearance. In its unlocked position at the distal end of the rigid tube, the collar engages neither the rigid tube nor the needle shield. When moved proximally within the proximally narrowing clearance, the collar reaches its locked position, where it force-lockingly engages the needle shield and the sheath, thereby locking the needle shield to the cap. As the needle shield needs not be moved relative to the cap when locked to the cap, the needle is protected during the assembling.

In an embodiment of the cap assembly, the sheath is formed as a rigid tube. The rigid tube is adapted to receive the collar loosely enclosing the needle shield in its unlocked position, wherein the collar is radially compressible. The collar is formed as a conical neck narrowing towards its distal end such that the collar is compressed by the sheath and force-lockingly engages the needle shield in its locked position when the sheath is moved proximally.

In some implementations, as an advantage, no force is exerted upon the needle shield along the longitudinal direction when locking the cap to the needle shield. In some implementations, as a further advantage, the collar may be pre-assembled to a case encasing the injection device with the needle protected by the needle shield. It is, however, also possible to pre-assemble the collar to the cap according to this embodiment. Thereby, the flexibility in manufacturing is improved.

In an embodiment of the cap assembly, the needle shield is formed as a rigid needle shield being made of a substantially rigid material. In another embodiment of the cap assembly, the needle shield is formed as a flexible needle shield being made of a flexible material such as rubber.

According to the disclosure, a method for assembling a cap assembly with a cap with a sheath formed by radially deflectable arms comprises the steps of
  slipping the collar over the radially deflectable arms in the distal direction towards the bottom,
  radially outwardly deflecting the radially deflectable arm,
  distally introducing the needle shield into the opening enclosed by the outwardly deflected radially deflectable arms until the recesses face the clips,
  releasing the radially deflectable arms to bring the clips into engagement with the corresponding recesses, and
  sliding the collar in the proximal direction until it force-lockingly engages the radially deflectable arms in its locked position.

In some implementations, as an advantage, according to this method, a cap assembly can be assembled without exerting force in the longitudinal direction upon the needle shield, thereby protecting the needle and improving sterility.

According to the disclosure, a method for assembling a cap assembly with a cap with a sheath formed as a rigid tube circumferentially enclosing the collar and adapted to receive the needle shield with a tubular, proximally narrowing clearance comprises the steps of
  sliding the collar in the distal direction until it faces the distal end of the sheath,
  distally introducing the needle shield into the sheath until it engages the sheath, and
  sliding the collar in the proximal direction until it force-lockingly engages the sheath and the needle shield.

In some implementations, as an advantage, according to this method, the needle shield is held by the cap when being locked to the cap, thereby protecting the needle and improving sterility. Further, the friction force will cause the collar to grip harder as the needle shield is removed from the needle during cap removal. In some implementations, as a further advantage, the one cap can fit a multitude of needle shields by adjustment of the collar, resulting in an improved platform flexibility.

According to the disclosure, a method for assembling a cap assembly with a cap with a sheath formed as a rigid tube adapted to receive the collar circumferentially enclosing the needle shield, wherein the collar is formed as a conical neck narrowing towards its distal end, comprises the steps of
  distally introducing the needle shield with the collar into the sheath until the distal end of the collar faces the proximal end of the sheath, and
  sliding the cap over the collar enclosing the needle shield in the proximal direction until the collar force-lockingly engages the needle shield and the sheath.

In some implementations, as an advantage, according to this method, a cap assembly can be assembled without exerting force in the longitudinal direction upon the needle shield, thereby protecting the needle. In some implementations, as a further advantage, such a method is applicable to collars that are pre-assembled to a case encasing the injection device with the needle protected by the needle shield as well as to collars that are pre-assembled to a cap that is to be mounted onto such a needle shield. Thereby, the flexibility in manufacturing such cap assemblies is improved.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
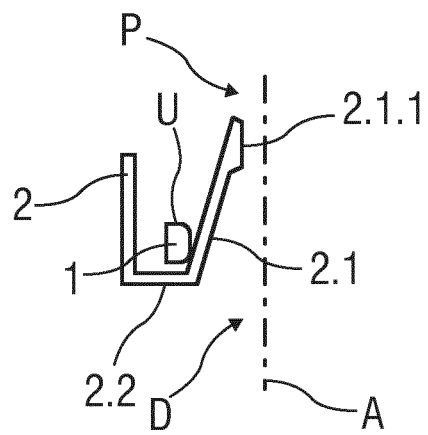
FIGS. 1A-1C show sectional views of an example of a cap assembly with a collar assembled to a cap with radially deflectable arms.
Figure 1B:
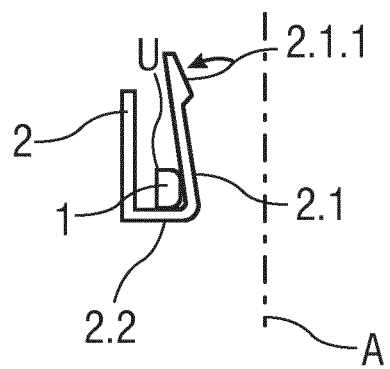
Figure 1C:
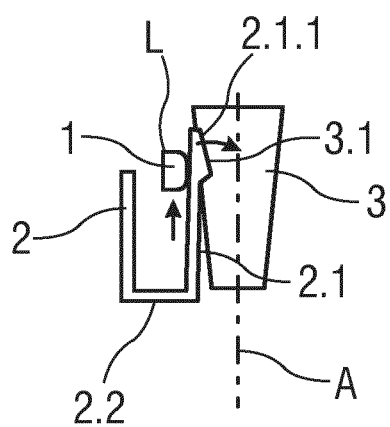

FIGS. 1A to 1C show an embodiment of a cap assembly with a collar 1 assembled to a cap 2. The cap 2 has an inner sheath that is formed by at least two radially deflectable arms 2.1. The cap 2 may be moulded, wherein the radially deflectable arms 2.1 are moulded such that the inner sheath narrows towards a proximal end P of the cap 2, as shown in FIG. 1A.

On their proximal ends, the radially deflectable arms 2.1 provide clips 2.1.1 that radially inwardly protrude towards a central longitudinal axis A of the cap assembly. The clips 2.1.1 may be formed as catches pointing towards the proximal end P, but other profiles adapted to form-fittingly lock with corresponding recesses are possible for the clips 2.1.1 as well.

The cap 2 has a bottom 2.2 on a distal end D. The collar 1 is assembled to the cap 2 such that it circumferentially encloses the radially deflectable arms 2.1. The collar 1 is assembled in an unlocked position U at the bottom 2.2 of the cap 2. It is also possible that the collar 1 is slid over the radially deflectable arms 2.1 towards its unlocked position U at the bottom 2.2 in a preparatory step of the assembling of the cap assembly.

FIG. 1B shows the cap 2 with the radially deflectable arms 2.1 forced apart radially outwardly in a subsequent step of assembling, thereby opening a circular clearance around the central longitudinal axis A. The circular clearance is adapted to receive the distal end of a rigid needle shield 3 covering a needle 4 of an injection device such as an autoinjector.

As shown in FIG. 1C, such a rigid needle shield 3 is introduced into the opening enclosed by the radially outwardly forced apart radially deflectable arms 2.1. The needle shield 3 is substantially conically narrowing towards its distal end such that it can be introduced into the cap 2 without application of force. The needle shield 3 provides recesses 3.1 in its mantle surface that are formed such that they can form-fittingly receive the clips 2.1.1 of the radially deflectable arms 2.1.

Once the recesses 3.1 face the corresponding clips 2.1.1, the radially deflectable arms 2.1 are released, such that the clips 2.1.1 form-fittingly engage the corresponding recesses 3.1. The recesses 3.1 are formed into the mantle surface of the needle shield 3 such that the radially deflectable arms 2.1 are slightly spread radially outwardly on their proximal ends. Therefore, when the collar 1 is moved towards the proximal end P of the cap 2 into a locked position L, it force-lockingly engages the radially deflectable arms 2.1 by friction. The collar 1 is thereby prevented from sliding back towards the bottom 2.2 of the cap 2 and the clips 2.1.1 are locked into the corresponding recesses 3.1, thereby locking the needle shield 3 to the cap 2. Thus, upon pulling the cap 2 in a distal direction, the needle shield 3 is removed from the needle 4.

Figure 2A:
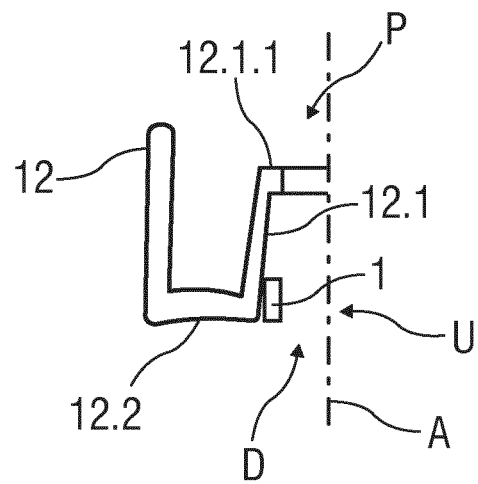
FIGS. 2A-2B show sectional views of an example of a cap assembly with a collar assembled to a cap with a rigid tube.
Figure 2B:
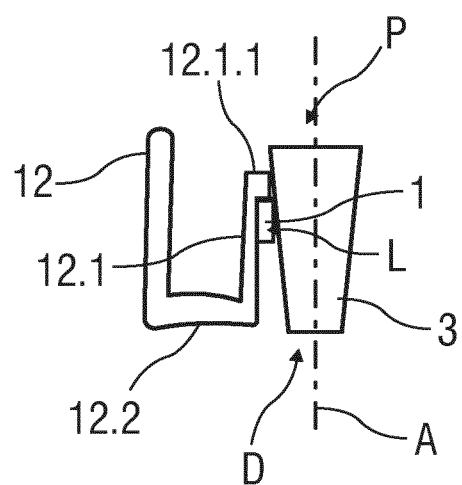

FIGS. 2A-2B show a further embodiment of a cap assembly with a collar 1 assembled to a cap 12. The cap 12 has an inner sheath formed as a cylindrical rigid tube 12.1 with a radially inwardly protruding stop 12.1.1 on its proximal end P. The radially inwardly protruding stop 12.1.1 may be formed as a circumferential flange, yet other embodiments such as inwardly protruding ribs are possible as well. The collar 1 is led inside the rigid tube 12.1 along the central longitudinal axis A, wherein the stop 12.1.1 prevents the collar 1 from leaving the tube 12.1 on the proximal end P. Upon assembling the cap assembly, the collar 1 is in its unlocked position U on the distal end D of the rigid tube 12.1.

The stop 12.1.1 is formed as to receive a conically narrowing distal end of the needle shield 3, as shown in FIG. 2B. In a first assembling step, the needle shield 3 is introduced into the rigid tube 12.1 in a distal direction, until the stop 12.1.1 engages the needle shield 3. A gap opens between the conical mantle surface of the needle shield 3 and the cylindrical inner surface of the rigid tube 12.1, wherein the clearance of this gap is sufficient to receive the collar 1 on the distal end, yet tighter than the collar 1 on the proximal end. In a second assembling step, the collar 1 is sled in a proximal direction along the central longitudinal axis A until it force-lockingly engages the needle shield 3 and the inner surface of the rigid tube 12.1 in a locked position L, thereby locking the needle shield 3 to the cap 2. Thus, upon pulling the cap 12 in a distal direction, the needle shield 3 is removed from the needle 4.

Figure 3A:
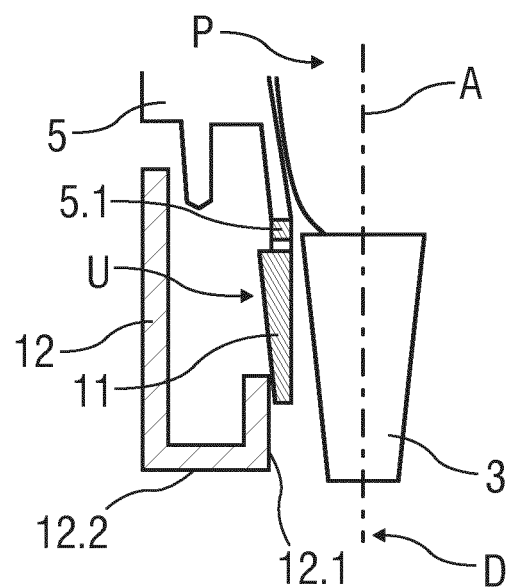
FIGS. 3A-3B show sectional views of an example of a cap assembly with a collar assembled to a case.
Figure 3B:
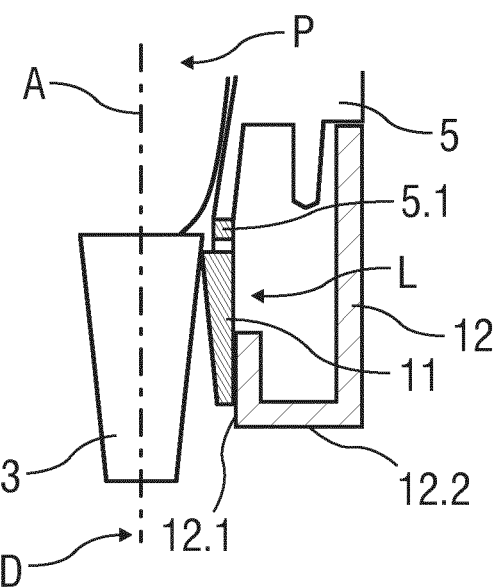

FIGS. 3A-3B show a cap assembly with a collar 11 assembled to a case 5 of an injection device such as an autoinjector. The collar 11 encloses a needle shield 3. The collar 11 is assembled to the distal end of the case 5 by means of a releasable holding 5.1. The collar 11 is formed as a conical neck with a wedge-shaped cross-section that narrows in the distal direction. The collar 11 is formed such that it can be compressed radially. For example, the collar 11 may be made from an elastic material such as rubber, wherein the compression is achieved using a tool inserted from the open end of the cap 12. The cap 12 may, for example, provide a small undercut and/or a rough surface finish in its side wall that, together with radial pressure caused by an axial compression, effects to hold the collar 11 in its position. In its unlocked position U, the collar 11 in its uncompressed state does not engage the needle shield 3.

The cap 12 has an inner sheath formed as a cylindrical rigid tube 12.1 and a bottom 12.2 on its distal end D. The bottom 12.2 may have a central opening aligned with the rigid tube 12.1, such that the rigid tube 12.1 is open on its distal end. The bottom 12.2 may also be formed as a continuous surface closing the cap 12 and the rigid tube 12.1 on the distal end D of the cap 12.

The clearance of the rigid tube 12.1 is sufficient to receive the distal end of the collar 11 circumferentially enclosing the needle shield 3, as shown in FIG. 3B. By sliding the cap 12 over the collar 11 in a proximal direction, the collar 11 is radially inwardly compressed due to its wedge-shaped profile, causing the releasable holding 5.1 to release the collar 11 from the case 5 such that it moves into its locked position L. In its locked position L, the compressed collar 11 force-lockingly engages the needle shield 3 and the inner surface of the rigid tube 12.1, thereby locking the needle shield 3 to the cap 12. Thus, upon pulling the cap 12 in a distal direction, the needle shield 3 is removed from the needle 4.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, autoinjector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1, 11 collar
2, 12 cap
2.1 deflectable arm, sheath
2.1.1 clip
2.2, 12.2 bottom
3 needle shield
3.1 recess
4 needle
5 case
5.1 holding
12.1 rigid tube, sheath
12.1.1 stop
A central longitudinal axis
D distal end
L locked position
P proximal end
U unlocked position

The invention claimed is:

1. An arrangement comprising:
a cap assembly for covering a needle shield of an injection device, wherein the cap assembly comprises:
a collar; and
a cap with a sheath and a bottom, the collar being attached to the cap,
wherein the collar, when attached to the cap, is movable along a longitudinal direction relative to the sheath from an unlocked position not engaging the sheath towards a locked position,
wherein, in the locked position, the sheath is force-lockingly engaged with the collar to lock the sheath to the needle shield,
wherein the collar is radially compressible, and
wherein the arrangement further comprises the needle shield.

2. The arrangement according to claim 1, wherein the sheath is formed by radially deflectable arms proximally extending from the bottom with radially protruding clips on proximal ends of the radially deflectable arms.

3. The arrangement according to claim 2, wherein the clips are configured to be received by corresponding recesses in an outer surface of the needle shield.

4. The arrangement according to claim 3, wherein the collar circumferentially encloses the radially deflectable arms such that the clips are form-fittingly held in the corresponding recesses when the collar is moved proximally towards the locked position.

5. The arrangement according to claim 1, wherein the sheath is formed as a rigid tube circumferentially enclosing the collar.

6. The arrangement according to claim 1, wherein the sheath is formed as a rigid tube configured to receive the collar engaging the needle shield in the unlocked position.

7. The arrangement according to claim 6, wherein the collar is formed as a conical neck narrowing towards a distal end of the collar such that the collar is radially compressed by the sheath and force-lockingly engages the needle shield in the locked position when the sheath is moved proximally.

8. The arrangement according to claim 1, wherein the needle shield is formed as a rigid needle shield.

9. The arrangement according to claim 1, wherein the needle shield is formed as a flexible needle shield.

10. A method of assembling the arrangement according to claim 5, the method comprising:
sliding the collar in a distal direction until the collar faces a distal end of the sheath; distally introducing the needle shield into the sheath until the needle shield engages the sheath; and
sliding the collar in a proximal direction until it force-lockingly engages the needle shield and the inner surface of the rigid tube in a locked position, thereby locking the needle shield to the cap.

11. A method of assembling an arrangement according to claim 4, the method comprising:
moving the collar over the radially deflectable arms in a distal direction;
radially outwardly deflecting the radially deflectable arms;
distally introducing the needle shield into an opening enclosed by the outwardly deflected radially deflectable arms until the recesses face the clips;
releasing the radially deflectable arms to bring the clips into engagement with the corresponding recesses; and
sliding the collar in a proximal direction until the collar force-lockingly engages the radially deflectable arms in the locked position.

12. A method of assembling the arrangement according to claim 7, the method comprising:
distally introducing the needle shield with the collar into the sheath until the distal end of the collar faces a proximal end of the sheath; and
sliding the cap over the collar enclosing the needle shield in a proximal direction until the collar engages the needle shield and the sheath.

* * * * *